(12) United States Patent
Neumann

(10) Patent No.: US 7,749,747 B2
(45) Date of Patent: Jul. 6, 2010

(54) PROCESS FOR SURFACE ACTIVATION AND/OR DEVULCANISATION OF SULFUR-VULCANIZED RUBBER PARTICLES

(75) Inventor: Willi Neumann, Bad Dueben (DE)

(73) Assignee: Cristallo Holdings, Inc., Edmonton (CA)

( * ) Notice: Subject to any disclaimer, the term of this patent is extended or adjusted under 35 U.S.C. 154(b) by 983 days.

(21) Appl. No.: 10/551,664

(22) PCT Filed: Mar. 29, 2004

(86) PCT No.: PCT/IB2004/000932

§ 371 (c)(1),
(2), (4) Date: Jun. 21, 2006

(87) PCT Pub. No.: WO2004/087799

PCT Pub. Date: Oct. 14, 2004

(65) Prior Publication Data

US 2007/0009997 A1    Jan. 11, 2007

(30) Foreign Application Priority Data

Apr. 1, 2003   (DE) ................................ 103 14 893

(51) Int. Cl.
*A62D 3/00* (2007.01)
*C10G 32/00* (2006.01)
(52) U.S. Cl. .................... 435/282; 435/262.5; 435/822
(58) Field of Classification Search ........................ None
See application file for complete search history.

(56) References Cited

U.S. PATENT DOCUMENTS 5,506,283 A * 4/1996 McInnis et al. .......... 525/332.8
5,518,619 A * 5/1996 Buisman ..................... 210/611
5,597,851 A * 1/1997 Romine et al. ................ 521/41
6,217,766 B1   4/2001 Stetter et al.
6,479,558 B1   11/2002 Fliermans

FOREIGN PATENT DOCUMENTS

| DE | 4042009 | * | 6/1992 |
| DE | 4425049 | * | 1/1996 |
| DE | 19607281 | * | 8/1997 |
| DE | 19728036 | * | 7/1999 |
| EP | 493732 | * | 12/1991 |
| IT | 402067 | | 11/1933 |
| JP | 54100441 | | 8/1979 |
| JP | 02-076575 | | 3/1990 |
| JP | 04--305282 | | 10/1992 |
| JP | 2002-275307 | | 9/2002 |

OTHER PUBLICATIONS

Bredberg et al, "Anaerobic desulfurization of ground rubber with the thermophilic archaeon Pyrococcus furiosus-a new method for rubber recycling", Appl. Microbiol. Biotechnol (2001) 55:pp. 43-48.*

* cited by examiner

*Primary Examiner*—David M. Naff
*Assistant Examiner*—Debbie K Ware
(74) *Attorney, Agent, or Firm*—Workman Nydegger

(57) ABSTRACT

Process for surface activation and/or devulcanization of sulfur-vulcanized rubber particles. In order to break the sulfur bridges and to reduce the sulfur, the rubber particles are treated in a biotechnological manner in a medium with mesophilic anaerobic and/or optionally anaerobic and/or microaerophilic bacteria and/or with one or more enzyme systems of such bacteria. The thus-treated activated rubber particles show improved vulcanization properties in comparison with non-treated rubber particles, and permit the production of better quality articles.

18 Claims, No Drawings

PROCESS FOR SURFACE ACTIVATION AND/OR DEVULCANISATION OF SULFUR-VULCANIZED RUBBER PARTICLES

BACKGROUND OF THE INVENTION

1. Field of the Invention

The invention relates to a process for surface activation and/or devulcanization of sulfur-vulcanized rubber particles.

2. Background and Related Art

Different processes are known from DE 4425049 C1, DE 19607281 A1, U.S. Pat. No. 5,506,283 for activation of comminuted scrap rubber and waste rubber. These processes are based either on physical or chemical operating principles or a combination of the two operating principles.

Processes are further known from DE 4042009 C2, EP 0493732 B1, U.S. Pat. No. 5,597,851 and DE 19728036 A1 for microbial and enzymatic activation of powdered rubber and rubber granulate.

A process is disclosed in the documents DE 4042009 C2 and EP 0493732 B1 which is based on microbial oxidation of the polysulfide bonded sulfur in rubber vulcanization. The oxidation of the polysulfide sulfur on the surface of the rubber particles takes place by means of chemolithotropic microorganisms in a bacterial suspension with a defilled supply of oxygen. The bacteria belong to the *Thiobacillus* genus. The oxidation of the sulfur is generally carried out up to the sulfate stage. The end product of the process is a replasticized, low-sulfur rubber material with good suitability for vulcanization.

A similar process is disclosed in U.S. Pat. No. 5,597,851. The particularity of this process consists, on the one hand, in that the thermophilic optionally chemolithotropic Sulfolobus acidocaldarius is primarily used as a sulfur oxidizing microorganism and, on the other hand, the treatment of the rubber particles is carried out merely with the enzyme system of this microorganism. The rubber particles themselves are not in direct contact with the microorganisms.

A process is disclosed in DE 19728036 A1 in which by biotechnological treatment of vulcanized rubber particles by means of defined reaction times/duration of oxidation, specific reactive functional groups in the form of hydroxyl groups, epoxy groups and carboxyl groups are produced on the particle surface. As a result, it is possible to vulcanize the activated powdered rubber and rubber granulate with different plastics, bitumens and other polymers. Bacteria of the *Thiobacillus* genus are also used for the microbial oxidation.

The previously known processes for microbial activation of powdered rubber and rubber granulate by sulfur oxidation comprise the following important disadvantages:

1. These activation processes are based on oxidation processes. In addition to the desired oxidation of the polysulfide sulfur, undesired oxidation of the polymer chains (attachment of free radicals) inevitably takes place simultaneously. The points on the particle surface which are still bonding-active are practically eliminated. The degree of degradation depends, amongst others, on the type of rubber (number of double bonds), the reaction temperature, the duration of the reaction and the concentration of dissolved oxygen in the suspension.
2. The degradation to the polymer chains causes, amongst others, an undesired release of specific rubber constituents (plasticizers, carbon black, zinc oxide, etc.).
3. In order to avoid foreign contamination, the processes have to be carried out at very low pH values (1 to 3) which necessitates additional requirements for the materials of the bioreactors and for the waste water treatment.

These disadvantages can be avoided by anaerobic processes. Such a process is known from Bredberg (K. Bredberg, J. Perssom, M. Christiansson, B. Stenberg, O. Holst: Anaerobic desulfurization of ground rubber with the thermophilic archaeon Pyrococcus furiosus—a new method for rubber recycling in the journal Appl. Microbiol. Biotechnol. (2001) 55, pages 4348), by using the sulfur-reducing, anaerobic, hyperthermophilic archaeon, Pyrococcus furiosus. This process nevertheless has the following disadvantages—in particular due to the hyperthermophilic characteristic of the archaeon:

1. The treatment of the powdered rubber over a lengthy period at a temperature range of 90-]00° C. leads to degradation of the polymer chains of the elastomers and thus to deterioration of the significant material technical parameters (tensile strength, elongation at break, abrasion, etc.).
2. Due to the high temperature exposure of the powdered rubber, increased rubber constituents are released (plasticizers, carbon black, zinc oxide, chemical protective agents, etc.) which have a toxic effect on the microorganisms and thus restrict the process of desulfurization or lead to a breakdown of the process.
3. Carrying out the process at such a high temperature range is uneconomical with regard to large-scale production and of ecological concern (release of toxic materials into the process waste water).

BRIEF SUMMARY OF THE INVENTION

The object of the invention, therefore, is to provide a method for surface activation and/or devulcanization of sulfur-vulcanized rubber particles which is carried out substantially at temperatures below 90° C. and avoids the aforementioned disadvantages of microbial oxidation processes.

DETAILED DESCRIPTION OF THE PREFERRED EMBODIMENTS

This object is achieved according to the invention by a process with the features of claim 1. Advantageous developments and embodiments are provided in the claims dependent on claim 1.

The invention is based on the consideration that a process for surface activation and/or devulcanization of sulfur-vulcanized rubber particles is provided, in which in order to break the sulfur bridges and to reduce the sulfur, the rubber particles are treated in a biotechnological manner in a medium with mesophilic anaerobic and/or mesophilic optionally anaerobic and/or mesophilic microaerophilic bacteria and/or one or more enzyme systems of such bacteria. Bacteria which can exist both with and without oxygen are understood by the term optionally anaerobic bacteria.

The essential difference from the process disclosed in Bredberg lies in the use of mesophilic microorganisms. The optimal living conditions of mesophilic bacteria are at 20 to 45° c. Thus the process according to the invention functions at temperatures markedly below 90° c. As a result, the aforementioned disadvantages of treatment with hypellhermophilic microorganisms are removed or at least greatly reduced. As the bacteria used in the process according to the invention are moreover anaerobic and/or optionally anaerobic and/or microaerophilic bacteria, the process functions by excluding oxygen or with very low concentrations of oxygen. As a result, the aforementioned disadvantages of the microbial oxidation process are avoided.

The operating principle of this treatment of the rubber particles according to the process of the invention, consists in the microorganisms breaking the sulfur bridges of the vulcanized rubber on the particle surface and partially or completely reducing the sulfur, without thereby degrading the polymer chains of the elastomers. By means of the process according to the invention, activated rubber particles are produced which, in comparison with nonactivated rubber particles, provide a high vulcanization capability. As a result, it is possible by using such activated rubber particles, in particular in the form of powdered rubber and rubber granulate to produce high quality products.

The treatment of the rubber particles during the process according to the invention can be microbial and/or enzymatic. In the case of an enzymatic process the treatment is, in particular, carried out exclusively by the enzyme system of the bacteria, preferably isolated from the bacteria.

By the term microbial treatment is understood that the bacteria themselves come into contact (interaction) with the surface of the rubber particles. During enzymatic treatment, however, the treatment, i.e. breaking the sulfur bridges and/or reducing the sulfur, is carried out only by the enzyme system or enzyme systems of the bacteria.

In detail, an enzymatic treatment can be carried out in the following manner: firstly the bacteria are grown in a preculture without contact with the sulfur-vulcanized rubber particles to be treated, by using a further sulfur substrate, for example elemental sulfur. Subsequently, the bacteria are broken down and the enzyme system is isolated (harvested) by generally known processes. The treatment of the sulfur-vulcanized rubber particles is then carried out exclusively by the isolated enzyme system.

It is, however, also possible that the bacteria produce the enzyme system in situ, i.e. the enzyme system required for the enzymatic treatment is not previously isolated.

Usefully, the medium for treating the rubber particles contains water, nutrients, a carbon source and bacteria or consists thereof and is therefore a suspension. An advantageous development provides that the concentration of the rubber particle material in the medium is substantially maintained below 35 percent by mass. Higher rubber particle concentrations cause problems when intermixing the reaction mass, during mass transfer and during bacterial growth, for example due to higher concentrations of toxic chemical substances, in particular antioxidants.

It can timber be provided that the medium for reducing temperature and/or concentration gradients is intermixed. Preferably the intermixing is carried out carefully, for example by means of an agitator.

A further useful variant of the process according to the invention provides that the treatment is carried out under anaerobic or microaerophilic conditions. Moreover it can be provided that the treatment is carried out substantially at temperatures below 90 DC, in particular below 50 DC, preferably within an optimal temperature range for mesophilic bacteria, which is approximately at 20 to 45° c. The treatment is preferably carried out at temperatures in a range of 33 to 37 DC.

As a result, the treatment of rubber particles is carried out as a whole under conditions which are optimally suited to the living conditions of the mesophilic anaerobic and/or mesophilic optionally anaerobic and/or mesophilic microaerophilic bacteria. Moreover, the aforementioned disadvantages of the known processes are substantially prevented thereby.

According to a development of the process, the pH value lies in the range of 5 to 9, in particular from 6 to 8. Moreover, the residence dwell time of the rubber particles can be in the region of 4 to 8 days, in particular from 5 to 7 days, preferably approximately 6 days.

Optimally successful desulfurization is in particular achieved by observing the following process parameters and conditions:

| | |
|---|---|
| Process temperature: | 33 to 37° C. |
| pH value: | 6 to 8 |
| Intermixing regime: | Careful intermixing by means of an agitator |
| Mean residence time: | 6 days |
| Particle size of rubber particles: | 0.2 to 0.4 mm |

A useful development of the process according to the invention provides that the bacteria used in the medium and/or for producing the enzyme system, are bacteria capable of sulfur respiration, i.e. sulfur reduction.

In tests it has been established that according to a corresponding adaptation phase, different anaerobic or optionally anaerobic or microaerophilic mesophilic bacteria are able to break the sulfur bridges in the vulcanized rubber and to reduce the sulfur. Positive results were achieved with, amongst others, the bacteria *Desulfuromonas thiophila*, *Desulfuromonas palmitatis*, *Sulfurospirillum deleyianum* and *Desulfuromonas acetoxidans*. Advantageously, bacteria are therefore used which substantially belong to one or more of these bacterial strains. Moreover, all or some of the bacteria are mixed populations.

Very good desulfurization rates are produced by the use of an anaerobic mesophilic mixed population which, in addition to the sulfur reducing bacteria, provides significant proportions of methanogenic bacteria. This population was isolated from Saale river sediment and is characterized by particular stability.

An embodiment of the invention provides that, with the rubber particles to be treated, it substantially refers to rubber powder and/or powdered rubber and/or rubber granulate. By rubber powder and powdered rubber is understood a material with a particle diameter of less than 1 mm, by rubber granulate a material with a particle diameter of between ca. 1 mm and 5 mm. It is useful and advantageous when the particle size of the rubber particles to be treated is in the region of 0.1 to 0.6 mm, in particular from 0.2 to 0.4 mm, i.e. when it refers to rubber powder and powdered rubber.

Usefully, according to a development it is provided that the rubber particles to be treated are substantially rubber particles made up of sulfur-vulcanized rubber types or composites based on sulfur-vulcanized rubber types. The process according to the invention is essentially suited to surface activation and/or devulcanization of all sulfur-vulcanized rubber types, for example SBR (Styrol Butadiene Elastomer), NR (Natural Rubber), NBR (Acrylonitrile Butadiene Elastomer, Nitrile Rubber) and EPDM (Ethylene Propylene Diene Elastomer).

According to an advantageous development the rubber particles are produced from scrap rubber (for example old tyres, technical rubber products such as seals, sections, rubber mouldings, conveyor belts) and/or waste rubber (production waste of the rubber producing and rubber processing industry). In this manner the process according to the invention serves to reclaim scrap and/or waste rubber.

A further embodiment provides that the rubber particles to be treated are produced in a comminution process, in particular a peeling process and/or hot grinding and/or cold grinding and/or cryogenic grinding and/or wet grinding. It is particularly advantageous when, during the comminution process to produce the rubber particles, the temperature of the rubber particles remains so low, in particular substantially lower than 90 DC, that thermooxidative degradation of the rubber particles is substantially avoided.

A particularly advantageous development of the process according to the invention provides that the surface activation and/or devulcanization is substantially restricted to the rubber particle surface and/or layers close to the surface, in order not to alter the material properties of the main mass of the rubber particle material. The layer close to the surface should therefore be at most 300 nm thick. This means that the effect of mesophilic desulfurization is deliberately restricted to the particle surface and/or layers close to the surface.

Usefully, the treatment of the rubber particles is carried out in a bioreactor. A bioreactor is an apparatus for carrying out materials conversion with microorganisms in a reproducible and controlled manner. Moreover, it can further be provided that the addition of the rubber particles to be treated into the bioreactor and/or the removal of the rubber particles to be treated from the bioreactor is carried out continuously or quasi-continuously or discontinuously. Alternatively or additionally, it can be further provided that the bioreactor is operated such that when removing the treated rubber particles from the bioreactor, no or only small an101mts of bacteria and/or medium containing enzymes for treating the rubber particles are discharged therewith and/or come into contact with atmospheric oxygen. This can be achieved by sedimentation and subsequent removal of the rubber particles under anaerobic conditions.

Usefully, in the method the sulfur bridges contained in the rubber particles are at least partially broken by the treatment and the sulfur is transferred into one or more gas-forming reaction products. One of the gas-forming reaction products can be hydrogen sulfide. A particularly advantageous development provides that the hydrogen sulfide formed during the treatment of the rubber particles is continuously or quasi-continuously removed from the gas phase. As a result, inhibition and/or toxification of the bacteria can be prevented.

An advantageous development of the process according to the invention provides that the treated rubber particles are washed with water after treatment, in particular to reduce salt loading, and subsequently are carefully dried, in particular substantially at temperatures below 90° C.

A further embodiment provides that rubber particles surface activated by means of the treatment, in particular powdered rubber, are produced which are used to manufacture rubber products. In this connection, these new rubber products can be substantially manufactured either only from treated surface activated rubber particles or from surface activated rubber particles with admixed virgin rubber, in particular by means of chemical vulcanization.

It can further be provided that rubber particles surface activated by means of the treatment, in particular powdered rubber, are produced which are used to manufacture elastomer alloys, in particular by phase coupling with plastics, preferably Polypropylene (PP) and/or Polyurethane (PU).

In addition to improving the material properties of the rubber products manufactured in this manner, the use of such surface activated rubber particles also results in a reduction of the specific product costs.

For example, the admixing of scrap powdered rubber activated according to the process according to the invention with virgin rubber, in comparison with admixing untreated powdered rubber, leads to a significant improvement of the material technical parameters of the resulting product, in particular the stress-strain behavior, the tear growth resistance and the impact resilience. It can further be established that by compounding thus activated scrap powdered rubber and EPDM powdered rubber with thermoplastics, in particular with Polypropylene—materials are produced of which the mechanical physical properties approach those of thermoplastic elastomers. In particular, an improvement can be seen in the elasticity compared to the use of comparable untreated scrap powdered rubber. This indicates that it results in intensive interdiffusion of the chains of the polymer phase and the elastomer phase and possibly also chemical vulcanization of the two phases (intensive phase coupling).

The invention is further described hereinafter with reference to an embodiment.

Cryogenically milled EPDM powdered rubber, with a particle size of less than 0.4 mm, is subjected to microbial surface vulcanization under anaerobic conditions. With an activation period of 8 days a level of desulfurization of the rubber is achieved of circa 4%. The microbial activated powdered rubber and non-activated powdered rubber of the same gross sample are respectively mixed and vulcanized with EPDM-virgin rubber at the ratio 1:1.

The tensile strength and the elongation at break of the respective end products and—by comparison—of EPDM virgin rubber are shown in the following table:

| End product vulcanized from: | Tensile Strength in MPa | Elongation at Break in % |
|---|---|---|
| EPDM - Virgin rubber (without admixing powered rubber) | 28 | 595 |
| 50% EPDM - Virgin rubber + 50% activation powdered rubber | 25 | 555 |
| 50% EPDM - Virgin rubber + 50% non-activated powdered rubber | 17.5 | 385 |

The comparison of the given values for the significant material parameters of tensile strength and elongation at break clearly shows that treatment according to the invention of rubber particles, i.e., in the example considered, microbial activation carried out under anaerobic conditions of powdered rubber, leads to a considerable improvement of the material properties compared to non-treated rubber particles.

As a whole, therefore, the activated rubber particles treated according to the process according to the invention, show improved vulcanization properties, in comparison with non-treated rubber particles and permit the production of better quality articles.

The invention claimed is:

1. A process for devulcanization of sulfur-vulcanized rubber particles comprising:
    treating one or more sulfur-vulcanized rubber particles in a medium with bacteria selected from at least one of a strain of:
    (i) *Desulfuromonas thiophila*;
    (ii) *Desulfuromonas palmitatis*;
    (iii) *Sulfurospirillum deleyianum*; or
    (iv) *Desulfuromonas acetoxidans*;
    wherein:
    one or more sulfur bridges are broken and an oxidation state of the sulfur is reduced; and
    the treating is carried out at temperatures below 50° Celsius.

2. The process as recited in claim 1, wherein the medium for treating the rubber particles comprises water, nutrients, a carbon source, and the selected bacteria.

3. The process as recited in claim 1, further comprising intermixing the medium with an agitator to reduce at least one of the temperature or concentration gradients.

4. The process as recited in claim 1, further comprising carrying out the treating under one of anaerobic or microaerophilic conditions.

5. The process as recited in claim 1, wherein the treating is carried out at temperatures within a temperature range of from about 33° C. to about 37° C.

6. The process as recited in claim 1, wherein the treating is carried out at a pH value in the region of from about 5 to about 9.

7. The process as recited in claim 1, wherein a residence time of the rubber particles in the medium is from about 4 to about 8 days.

8. The process as recited in claim 1, wherein the bacteria belong to two or more of the *Desulfuromonas thiophila, Desulfuromonas palmitatis, Sulfurospirillum deleyianum,* or *Desulfuromonas acetoxidans* bacterial strains.

9. The process as recited in claim 1, wherein the rubber particles comprise any one or more of powdered rubber or rubber granulate, wherein the particle size of the powder or granulate is from about 0.1 mm to about 0.6 mm.

10. The process as recited in claim 1, wherein the rubber particles comprise a composite of sulfur-vulcanized rubber.

11. The process as recited in claim 1, wherein the rubber particles comprise rubber particles made of scrap rubber and/or waste rubber, such that the process reclaims the scrap and/or waste rubber.

12. The process as recited in claim 1, wherein the rubber particles are produced in any one of:

i) a comminution process, such as a peeling process;
ii) a hot grinding process;
iii) a cold grinding process;
iv) a cryogenic grinding process; or
v) a wet grinding process.

13. The process as recited in claim 1, wherein the devulcanization is substantially restricted to the rubber particle surface and/or layers close to the surface that have a thickness of up to 300 nm, in order to substantially avoid altering the material properties of the main mass of the rubber particle.

14. The process as recited in claim 1, wherein the treating of the rubber particles is carried out in a bioreactor.

15. The process as recited in claim 1, wherein the treating is carried out in any of a:

i) continuous fashion;
ii) quasi-continuous fashion; or
iii) discontinuous fashion.

16. The process as recited in claim 1, wherein during the treating, hydrogen sulfide is produced, and is at least quasi-continuously removed to avoid inhibition of the bacteria.

17. The process as recited in claim 1, further comprising:
after treating, washing the rubber particles with water to reduce salt loading; and
subsequently drying the washed rubber particles at temperatures below 90° C.

18. The process as recited in claim 1, wherein a concentration of the rubber particles in the medium is maintained below 35 wt-%.

* * * * *